United States Patent [19]

Arakawa

[11] Patent Number: 4,646,721
[45] Date of Patent: Mar. 3, 1987

[54] LIGHT SHIELDING CONSTRUCTION FOR THE FORWARD END OF AN ENDOSCOPE

[75] Inventor: Satoshi Arakawa, Omiya, Japan
[73] Assignee: Fuji Photo Optical Co., Ltd., Japan
[21] Appl. No.: 768,831
[22] Filed: Aug. 23, 1985

[30] Foreign Application Priority Data

Aug. 28, 1984 [JP] Japan ............................ 59-130217[U]
Aug. 28, 1984 [JP] Japan ............................ 59-130218[U]

[51] Int. Cl.⁴ ............................................. A61B 1/06
[52] U.S. Cl. ....................................................... 128/6
[58] Field of Search ................. 128/4, 6, 7, 8; 358/98

[56] References Cited

U.S. PATENT DOCUMENTS

| | | | |
|---|---|---|---|
| 2,788,390 | 4/1957 | Sheldon | 128/8 X |
| 3,924,608 | 12/1975 | Mitsui | 128/6 X |
| 4,266,534 | 5/1981 | Ogawa | 128/6 |
| 4,491,865 | 1/1985 | Danna et al. | 358/98 |
| 4,573,450 | 3/1986 | Arakawa | 128/6 |

FOREIGN PATENT DOCUMENTS 3233924 4/1983 Fed. Rep. of Germany ......... 128/6

Primary Examiner—William H. Grieb
Attorney, Agent, or Firm—Parkhurst & Oliff

[57] ABSTRACT

An endoscope includes in the viewing head of its insertable section into a cavity of a living body an image sensor for generating a video signal which in turn is transmitted to a television display to be visualized thereon as a television picture. The image sensor with a shape such as a plate is located in a plane containing the longitudinal center line of the viewing head.

According to the present invention, a mask having an opening formed at a position opposed to an image area of the image sensor is provided, so that any light other than the light contributing to the image formation can be prevented from falling into the image sensor.

4 Claims, 5 Drawing Figures

LIGHT SHIELDING CONSTRUCTION FOR THE FORWARD END OF AN ENDOSCOPE

BACKGROUND OF THE INVENTION

1. Field of the Invention

The present invention relates to an endoscope, and more particularly relates to an endoscope which has as an image pick-up device a plate like image sensor disposed within a viewing head thereof.

2. Description of the Prior Art

In addition to endoscopes having an optical fiber bundle as its image guide means, there have been proposed TV endoscopes of a type having as an image pick-up device an image sensor such as a charge coupled device (CCD) which comprises a great number of small photosensitive elements (pixels) arranged in matrix. Such TV endoscopes, which are far better than endoscopes heretofore used in terms of durability, the effect of video signal management and production cost, are still in the developmental stage.

In developing the TV endoscope, there are two objectives the first objective being to reduce the outer diameter of the endoscope to allow insertion of it into a cavity of a living body and the other requirement to improve the resolving-power i.e. increasing the number of picture elements on the image sensor. Accordingly, it becomes very important to efficiently arrange construction of the forward end section of the endoscope, particularly, the image sensor, or an objective lens assembly to make an optical image focus at the image sensor.

The inventor having as his objective the provision of a plate-shaped image sensor, has proposed an arrangement wherein: the plate-shaped image sensor is provided on a plane incorporating the center axis of the endoscope in the longitudinal direction; an objective lens assembly is disposed on one side of the plate-shaped image sensor, with the axial line of the objective lens assembly being in parallel to the plate-shaped image sensor; a right-angled prism is provided in the rear of the objective lens assembly to turn the light path at 90°, and a light emitting surface is cemented to the image sensor. With this arrangement, it has become possible to effectively utilize the outer diameter of the endoscope so as to provide an image sensor which is wide in width in the forward end portion having a small diameter.

Now, in order to observe an affected portion with the objective lens assembly, it is necessary to irradiate the affected portion by use of light guides. Because of this, light guides each formed on an optical fiber bundle or the like are provided on opposite sides of the objective lens assembly in parallel thereto in the forward end portion of the endoscope. In other words, the light guides are disposed close to a light receiving surface of the image sensor. It is possible that the light of the optical fiber bundle forming the light guide could leak to the light receiving surface of the image sensor. If any light other than the light from the objective lens assembly enters an image area forming the image pick-up area of the image sensor, then image pick-up function is hampered. If any light other than the light relating to the image formation enters a storage area acting as an image transferring area, then the transferring function is hampered. As the result, an accurate image may not be obtained or an image may be blurred due to a cause of blooming or the like.

SUMMARY OF THE INVENTION

The present invention has been developed to obviate the disadvantages of the prior art and has as its object the provision of an endoscope wherein light leaking from light guides is prevented from entering an image sensor disposed in the forward end portion of the endoscope, so that an accurate and clear image can be obtained.

The endoscope according to the present invention is of an arrangement wherein a mask having an opening formed at a position opposed to an image area of the image sensor is provided between the image sensor and an objective lens assembly. The present invention contemplates that the lights from the light guides and the like are prevented from falling into a light receiving surface of the image sensor by this mask, whereby blooming and the like are prevented from occurring.

The endoscope according to the present invention is constructed such that the exposed forward portions of the light guides positioned close to the image sensor are covered by light shielding materials. The present invention contemplates that the lights from the light guides are prevented from falling into the light receiving surface of the image sensor by the light shielding materials covering the light guides, to thereby prevent blooming or the like from occurring.

BRIEF DESCRIPTION OF THE DRAWINGS

The exact nature of this invention, as well as other objects and advantages thereof, will be readily apparent from consideration of the following description relating to the accompanying drawings, in which like reference characters designate the same or similar parts throughout the figures thereof and wherein.

DETAILED DESCRIPTION OF THE PREFERRED EMBODIMENT

Description will hereunder be given of the preferred embodiment of an endoscope according to the present invention with reference to the accompanying drawings.

Figure 1:
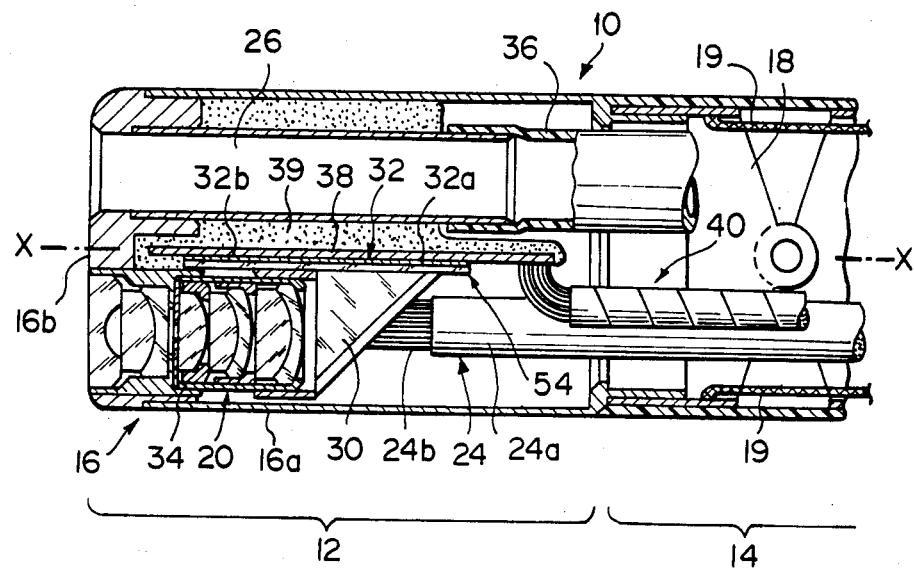
FIG. 1 is a longitudinal sectional view of an embodiment in which the present invention is applied to a front view type of endoscope.
Figure 2:
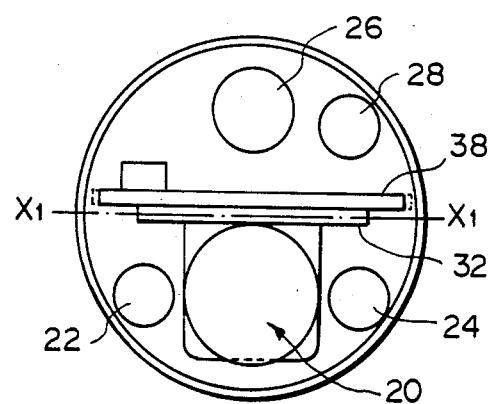
FIG. 2 is a schematic cross sectional view of the endoscope shown in FIG. 1.

Referring now to FIG. 1 shown therein in sectional form, is an embodiment in which the present invention is applied to a front view type of endoscope having a flexible section insertable into a cavity of a living body including in its forward end portion 10 a viewing head 12 and an intermediate bendable part 14. The viewing head 12, which has a metal barrel 16, is inflexible. The metal barrel 16 is comprised of a metal tube 16a forming a main portion of the viewing head 12 and a disc-shaped forward end portion 16b coupled to the forward end of the metal tube 16a. The bending part 14, comprieses a chain of rings 18 articulated to one another which is flexed in desired directions by the operation of flexure controlling wires (not shown) in a manner well known in the art. As seen from FIG. 2, there are incorporated within the forward end portion 10 various elements such as light guide means 22 and 24 made of an optical fiber bundle, a forceps channel 26, an air and water supplying channel 28 and an objective lens assembly 20, each element extending along the longitudinal axis of the flexible section (i.e., the horizontal direction in FIG. 1). As apparent from FIG. 1, in the rear of the objective lens assembly 20 generally comprising plural elements, there is provided a right-angled prism 30 for turning the optical axis of the objective lens assembly 20 at a right angle. The prism 30 has a light emitting surface to which a plate like, rectangular image sensor 32 is cemented.

The aforementioned arrangement of the image pick-up unit permits location of the image sensor plate 32 close to a plane containing the center line (shown by the line X—X in FIG. 1 and X1—X1 in FIG. 2), making it possible to use the limited space effectively. It should be noted that if a dustproof construction is not required, it is not always necessary to cement the image sensor plate 32 to the prism 30. Therefore, it is possible to dispose elements, for example a lens, a masking member and the like, between the image sensor plate 32 and the prism 30. In addition, a reflection mirror, disposed at about a right angle, may be substituted for the prism 30.

Provided in the forward end portion 16b of the metal barrel 16 are various channels, for example a forceps channel 26 coupled to a guide tube 36 through which a forceps is inserted into a cavity.

Figure 3:
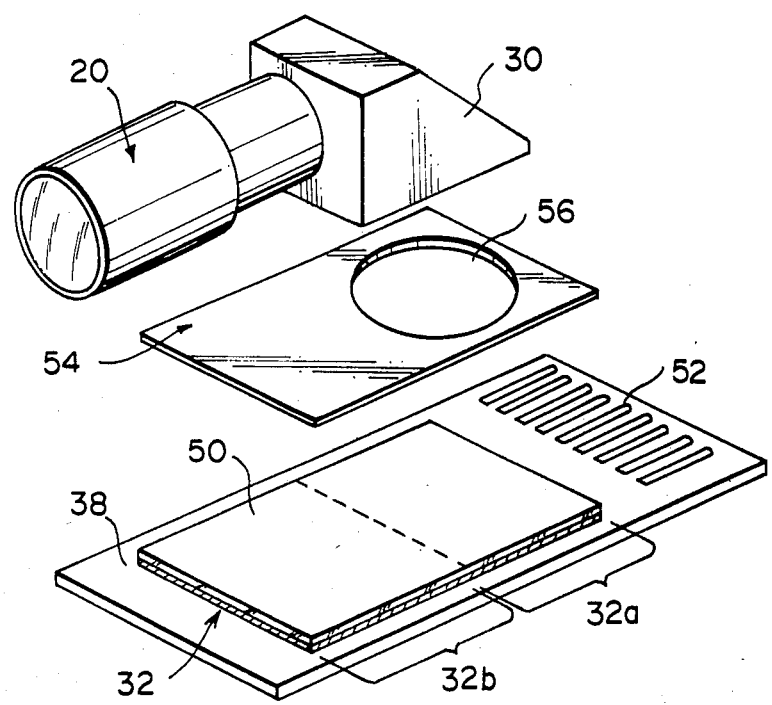
FIG. 3 is a disassembled perspective view showing the essential portions of a first embodiment of the present invention, with FIGS. 1 and 2 being turned upside down.

FIG. 3 is a perspective view showing in detail the cemented portion between the objective lens assembly 20 and the image sensor 32.

The image sensor 32 is constructed as a so-called rear surface inciding type, wherein an image pick-up surface of the solid state imaging device is cut off as a thin sheet, which is attached to the undersurface of a glass plate 50. The image sensor 32 is comprised of an image area 32a where an image is picked up from the light received from the prism 30, and a storage area 32b for transferring the image received by the image area 32a. A connector section 52 connected thereto with lead wires 40 is formed in the rear portion of a seating plate 38 of the image sensor 32. The lead wires 40 deliver a driving signal from a driving circuit of a control unit, not shown, to the image sensor 32, and deliver a video signal from the image sensor 32 to the control unit.

A mask 54 is interposed between this image sensor 32 and the objective lens assembly 20. The mask 54 is formed into a generally rectangular form so as to cover the glass plate 50 attached to the image sensor 32 and a round hole 56 is penetratingly provided at a portion thereof corresponding to a light path from the prism 30 to the image area 32a. In other words, the image pick-up surface of the image sensor 32 is shielded by the mask 54 such that no light enters the image pick-up surface other than an optical image obtainable through the prism 30 from the objective lens assembly 20, which falls into the image pick-up surface through the round hole 56.

Figure 4:
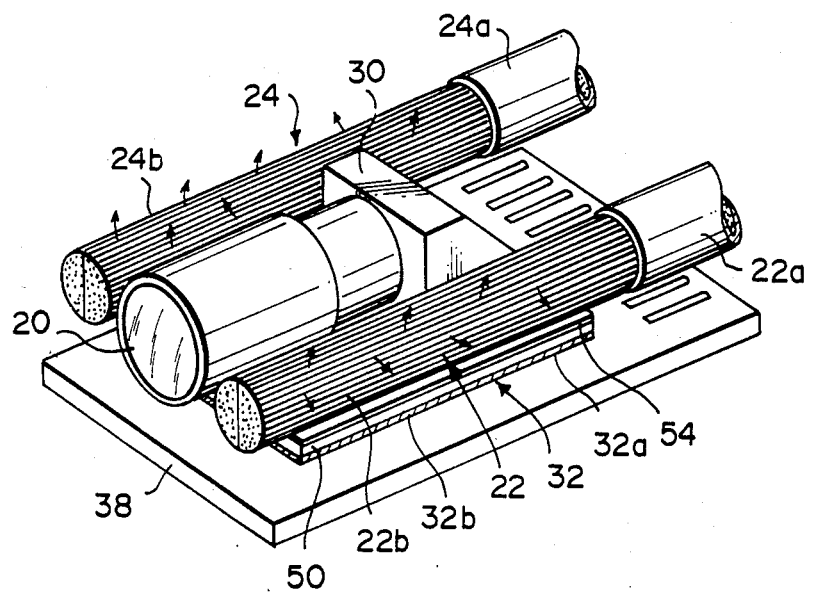
FIG. 4 is an assembled perspective view of a first embodiment shown in FIG. 3.

FIG. 4 is a perspective view showing the arrangement of the object lens assembly 20, image sensor 32, and light guides 22 and 24 after assembly. The light guides 22 and 24 are disposed at opposite sides of the objective lens assembly 20, with the axial lines thereof being parallel to the axial line of the objective lens assembly 20 so as to irradiate a portion of an object to be observed. These light guides 22 and 24 are each comprised of a bundle of optical fibers. Each of the light guides 22 and 24 is connected at the rear end thereof to a light source, not shown, and coupled at the forward end thereof to the metal barrel 16 of the endoscope and fixed thereto. Most parts of the optical fiber bundles are covered by tubes 22a l and 24a which are made of silicone rubber or the like. However, the optical fiber bundles are partially exposed from the tubes 22a and 24a because the forward end portions of the optical fiber bundles are coupled to openings of the metal barrel 16 and fixed thereto. The exposed portions 22b and 24b are hardened by epoxy resin or the like. Consequently, light leaks from the exposed portions 22b and 24b of the light guides 22 and 24, to the opposite sides of the objective lens assembly 20, i.e. the image pick-up surface of the image sensor 32. Thus, in the absence of a countermeasure, the light leaking from the light guides 22 and 24 enters the image sensor 32, where the light hampers the image pick-up function in the image area 32a and/or impede the transferring function in the storage area 32b.

However, the image pick-up surface of the image sensor 32, i.e. the surface of the image sensor 32 on the side of the objective lens assembly 20 is covered by the mask 54. Hence, the lights from the light guides 22 and 24 do not enter the image sensor 32. Consequently, the image area 32a picks up an image normally and no blooming occurs in the image normally transferred through the storage area, so that a satisfactory image can be obtained.

Furthermore, a heat conductive material 39 is interposed between the seating plate 38 and the metal barrel 16. The heat conductive material 39 can, for example, be obtained by mixing metal powder such as aluminum with epoxy resin. The heat conductive material 39 fills a portion of the assembly disposed upwardly of the seating plate 38 in FIG. 1.

The embodiment of the endoscope with the above-described arrangement according to the present invention is of such an arrangement that the mask 54 covering the image pick-up surface of the image sensor 32 is interposed between the image sensor 32 and the objective lens assembly 20, the round hole 56 is formed in a portion of the mask 54, into which the light from the prism 30 falls so that only the optical image obtained from the objective lens assembly 20 can be recieved, and light other than the light from the prism 30, particularly, the light from the light guides 22 and 24 disposed adjacent the objective lens assembly 20 is blocked. Consequently, any light other than the light contributing to the image formation on the image pick-up surface of the image sensor 32 is blocked, thus the image pick-up function in the image area 32a is not hampered and the transferring function in the storage area 32b is not impeded.

Figure 5:
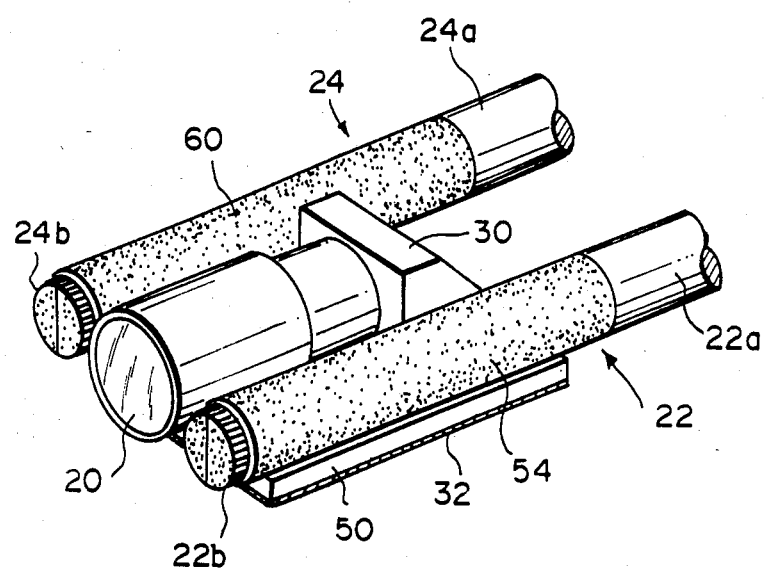
FIG. 5 is an assembled perspective view showing a second embodiment of the present invention.

FIG. 5 is a perspective view showing a second embodiment of the endoscope according to the present invention. As shown in FIG. 5, the forward end portions 22b and 24b of the light guides 22 and 24, which are exposed from the tubes 22a and 24a as shown in FIG. 4 are covered by light shielding materials 60, 54 whereby light is prevented from leaking from the light guides 22 and 24.

Metallic tubes made of aluminum foil, stainless steel and the like, or a coating of a light shielding coating material or resin, may be used as the light shielding material 60, 54.

Thus, in the second embodiment of the endoscope with the above-described arrangement according to the present invention, the forward exposed portions of the light guides 22 and 24 are covered by light shielding materials 60, 54 so that no light enters the image sensor 32 from the light guides 22 and 24 disposed adjacent the image sensor 32.

It should be understood, however, that there is no intention to limit the invention to the specific forms disclosed, but on the contrary, the invention is to cover all modifications, alternate constructions and equivalents falling within the spirit and scope of this invention as expressed in the appended claims.

What is claimed is:

1. An endoscope having an insertable flexible section, for displaying an object of interest on a screen of a television set in response to a video signal obtained from a plate-shaped image sensor provided in a forward end portion of the insertable flexible section of said endoscope comprising:

said plate-shaped image sensor provided on a plane incorporating the center axis of said insertable flexible section in the longitudinal direction of said endoscope;

light guides comprised of bundles of optical fibers provided in the forward end portion of the insertable flexible section of said endoscope for irradiating the object to be observed;

an objective lens assembly provided in said insertable flexible section of the endoscope; and a mask having an opening formed at a position opposed to an image area of said image sensor, said mask being interposed between said plate-shaped image sensor and said objective lens assembly.

2. An endoscope as set forth in claim 1, wherein a forward end portion of each of said bundles of optical fibers forming said light guides is exposed and the remaining portion of bundles are covered.

3. An endoscope wherein an object of interest is displayed on a screen of a television set in response to a video signal obtained from a plate-shaped image sensor provided in a forward end portion of said endoscope, comprising:

a plate-shaped image sensor provided on a plate incorporating the center axis of an insertable flexible section of said endoscope in the longitudinal direction;

an objective lens assembly provided in the insertable flexible section of the endoscope and including light guides formed of bundles of optical fibers having forward exposed portions, respectively, for irradiating the object to be observed; and light shielding materials for covering the forward exposed portions of said light guides.

4. An endoscope as set forth in claim 3, wherein said light shielding material includes metallic tubes or a coating of a light shielding coating material or resin.

* * * * *